(12) United States Patent
Huppert

(10) Patent No.: US 7,291,170 B2
(45) Date of Patent: Nov. 6, 2007

(54) INTERSOMATIC CAGE WITH UNIFIED GRAFTS

(75) Inventor: Jean Huppert, L'Etrat (FR)

(73) Assignee: LDR Medical, Troyes Cedex (FR)

( * ) Notice: Subject to any disclaimer, the term of this patent is extended or adjusted under 35 U.S.C. 154(b) by 0 days.

(21) Appl. No.: 10/276,712

(22) PCT Filed: May 18, 2001

(86) PCT No.: PCT/FR01/01545

§ 371 (c)(1),
(2), (4) Date: Mar. 26, 2003

(87) PCT Pub. No.: WO01/87194

PCT Pub. Date: Nov. 22, 2001

(65) Prior Publication Data

US 2003/0195626 A1    Oct. 16, 2003

(30) Foreign Application Priority Data

May 18, 2000  (FR) .................................. 00 06351

(51) Int. Cl.
*A61F 2/44* (2006.01)
(52) U.S. Cl. ................................................. 623/17.11
(58) Field of Classification Search ............. 623/17.11, 623/17.16
See application file for complete search history.

(56) References Cited

U.S. PATENT DOCUMENTS

| 4,714,469 | A | 12/1987 | Kenna |
| 4,997,432 | A | 3/1991 | Keller |
| 5,192,327 | A | 3/1993 | Brantigan |
| 5,246,458 | A | 9/1993 | Graham |
| 5,306,307 | A | 4/1994 | Senter et al. |
| 5,306,309 | A | 4/1994 | Wagner et al. |
| 5,397,364 | A | 3/1995 | Kozak et al. |
| 5,425,772 | A | * 6/1995 | Brantigan ................ 623/17.11 |
| 5,458,638 | A | 10/1995 | Kuslich et al. |
| 5,534,029 | A | 7/1996 | Shima |
| 5,554,191 | A | * 9/1996 | Lahille et al. ........... 623/17.11 |
| 5,609,636 | A | 3/1997 | Kohrs et al. |
| 5,713,899 | A | * 2/1998 | Marnay et al. ................ 606/61 |

(Continued)

FOREIGN PATENT DOCUMENTS

DE    3741493 A1    6/1989

(Continued)

OTHER PUBLICATIONS

U.S. Appl. No. 60/121,705, filed Feb. 25, 1999, Biscup.

(Continued)

*Primary Examiner*—Corrine McDermott
*Assistant Examiner*—Christopher Daniel Prone
(74) *Attorney, Agent, or Firm*—Fish & Richardson P.C.

(57) ABSTRACT

An intervertebral cage includes a thin main wall having two return parts at opposite ends of the wall. The wall has an approximately constant thickness. The return parts are extended by facing end parts having a gap between them. The wall, the return parts and end parts delimit an inner cavity. The gap extends parallel to the wall and has a length between 50% and 100% of the cavity length. The gap length is preferably between 70% to 90% of the cavity length.

23 Claims, 3 Drawing Sheets

U.S. PATENT DOCUMENTS

| | | |
|---|---|---|
| 5,741,253 A | 4/1998 | Michelson |
| 5,755,798 A | 5/1998 | Papavero et al. |
| 5,766,252 A | 6/1998 | Henry et al. |
| 5,772,661 A | 6/1998 | Michelson |
| 5,776,199 A | 7/1998 | Michelson |
| 5,782,919 A * | 7/1998 | Zdeblick et al. ......... 623/17.16 |
| 5,797,909 A | 8/1998 | Michelson |
| 5,800,550 A | 9/1998 | Sertich |
| 5,860,973 A | 1/1999 | Michelson |
| 5,865,845 A | 2/1999 | Thalgott |
| 5,888,223 A | 3/1999 | Bray |
| 5,888,224 A | 3/1999 | Beckers et al. |
| 5,984,967 A | 11/1999 | Zdeblick et al. |
| 6,001,130 A | 12/1999 | Bryan et al. |
| 6,033,438 A | 3/2000 | Bianchi et al. |
| 6,045,579 A | 4/2000 | Hochshuler et al. |
| 6,063,121 A | 5/2000 | Xavier et al. |
| 6,080,158 A | 6/2000 | Lin |
| 6,080,193 A | 6/2000 | Hochshuler et al. |
| 6,093,205 A | 7/2000 | McLeod et al. |
| 6,096,038 A | 8/2000 | Michelson |
| 6,096,080 A | 8/2000 | Nicholson et al. |
| 6,111,164 A | 8/2000 | Rainey |
| 6,113,637 A | 9/2000 | Gill et al. |
| 6,113,638 A | 9/2000 | Williams et al. |
| 6,120,502 A | 9/2000 | Michelson |
| 6,123,705 A | 9/2000 | Michelson |
| 6,136,031 A | 10/2000 | Middleton |
| 6,146,421 A | 11/2000 | Gordon et al. |
| 6,149,650 A | 11/2000 | Michelson |
| 6,156,067 A | 12/2000 | Bryan et al. |
| 6,179,875 B1 | 1/2001 | Von Strempel |
| 6,193,757 B1 | 2/2001 | Foley et al. |
| 6,206,922 B1 | 3/2001 | Zdeblick et al. |
| 6,210,412 B1 | 4/2001 | Michelson |
| 6,224,595 B1 | 5/2001 | Michelson |
| 6,235,059 B1 | 5/2001 | Benezech et al. |
| 6,241,770 B1 | 6/2001 | Michelson |
| 6,245,072 B1 | 6/2001 | Zdeblick et al. |
| 6,245,108 B1 | 6/2001 | Biscup |
| 6,251,140 B1 | 6/2001 | Marino et al. |
| 6,258,125 B1 | 7/2001 | Paul et al. |
| 6,264,656 B1 | 7/2001 | Michelson |
| 6,270,498 B1 | 8/2001 | Michelson |
| 6,277,149 B1 | 8/2001 | Boyle et al. |
| 6,296,664 B1 | 10/2001 | Middleton |
| 6,302,914 B1 | 10/2001 | Michelson |
| 6,306,170 B2 | 10/2001 | Ray |
| 6,315,797 B1 | 11/2001 | Middleton |
| 6,348,071 B1 | 2/2002 | Steffee et al. |
| 6,350,283 B1 | 2/2002 | Michelson |
| 6,364,880 B1 | 4/2002 | Michelson |
| 6,371,988 B1 | 4/2002 | Pafford et al. |
| 6,375,655 B1 | 4/2002 | Zdeblick et al. |
| 6,395,031 B1 | 5/2002 | Foley et al. |
| 6,395,035 B2 | 5/2002 | Bresina et al. |
| 6,402,750 B1 | 6/2002 | Atkinson et al. |
| 6,402,785 B1 | 6/2002 | Zdeblick et al. |
| 6,409,765 B1 | 6/2002 | Bianchi et al. |
| 6,419,704 B1 | 7/2002 | Ferree |
| 6,423,095 B1 | 7/2002 | Van Hoeck et al. |
| 6,432,106 B1 | 8/2002 | Fraser |
| 6,432,107 B1 | 8/2002 | Ferree |
| 6,447,512 B1 | 9/2002 | Landry et al. |
| 6,447,544 B1 | 9/2002 | Michelson |
| 6,447,547 B1 | 9/2002 | Michelson |
| 6,454,769 B2 | 9/2002 | Wagner et al. |
| 6,458,159 B1 | 10/2002 | Thalgott |
| 6,461,359 B1 | 10/2002 | Tribus et al. |
| 6,468,310 B1 | 10/2002 | Ralph et al. |
| 6,471,724 B2 | 10/2002 | Zdeblick et al. |
| 6,478,823 B1 | 11/2002 | Michelson |
| 6,482,233 B1 | 11/2002 | Aebi et al. |
| 6,500,205 B1 | 12/2002 | Michelson |
| 6,524,312 B2 | 2/2003 | Landry et al. |
| 6,527,806 B2 | 3/2003 | Ralph et al. |
| 6,540,785 B1 | 4/2003 | Gill et al. |
| 6,554,863 B2 | 4/2003 | Paul et al. |
| 6,576,016 B1 | 6/2003 | Hochshuler et al. |
| 6,579,291 B1 | 6/2003 | Keith et al. |
| 6,582,468 B1 | 6/2003 | Gauchet |
| 6,592,624 B1 | 7/2003 | Fraser et al. |
| 6,599,320 B1 | 7/2003 | Kuslich et al. |
| 6,605,089 B1 | 8/2003 | Michelson |
| 6,610,089 B1 | 8/2003 | Liu et al. |
| 6,610,092 B2 | 8/2003 | Ralph et al. |
| 6,613,091 B1 | 9/2003 | Zdeblick et al. |
| 6,616,671 B2 | 9/2003 | Landry et al. |
| 6,635,087 B2 | 10/2003 | Angelucci et al. |
| 6,645,206 B1 | 11/2003 | Zdeblick et al. |
| 6,645,249 B2 | 11/2003 | Ralph et al. |
| 6,652,584 B2 | 11/2003 | Michelson |
| 6,660,038 B2 | 12/2003 | Boyer, II et al. |
| 6,666,890 B2 | 12/2003 | Michelson |
| 6,669,730 B2 | 12/2003 | Ralph et al. |
| 6,669,731 B2 | 12/2003 | Ralph et al. |
| 6,673,113 B2 | 1/2004 | Ralph et al. |
| 6,676,703 B2 | 1/2004 | Biscup |
| 6,679,887 B2 | 1/2004 | Nicholson et al. |
| 6,679,915 B1 | 1/2004 | Cauthen |
| 6,695,851 B2 | 2/2004 | Zdeblick et al. |
| 6,695,882 B2 | 2/2004 | Bianchi et al. |
| 6,709,458 B2 | 3/2004 | Michelson |
| 6,716,247 B2 | 4/2004 | Michelson |
| 6,719,794 B2 | 4/2004 | Gerber et al. |
| 6,733,504 B2 | 5/2004 | Lin et al. |
| 6,733,531 B1 | 5/2004 | Trieu |
| 6,733,535 B2 | 5/2004 | Michelson |
| 6,736,850 B2 | 5/2004 | Davis |
| 6,740,117 B2 | 5/2004 | Ralph et al. |
| 6,740,118 B2 | 5/2004 | Eisermann et al. |
| 6,743,255 B2 | 6/2004 | Ferree |
| 6,743,256 B2 | 6/2004 | Mason |
| 6,743,257 B2 | 6/2004 | Castro |
| 6,749,636 B2 | 6/2004 | Michelson |
| 6,758,849 B1 | 7/2004 | Michelson |
| 6,767,367 B1 | 7/2004 | Michelson |
| 6,770,074 B2 | 8/2004 | Michelson |
| 6,793,679 B2 | 9/2004 | Michelson |
| RE38,614 E | 10/2004 | Paul et al. |
| 6,800,092 B1 | 10/2004 | Williams et al. |
| 6,800,093 B2 | 10/2004 | Nicholson et al. |
| 2001/0020185 A1 | 9/2001 | Ray |
| 2002/0082597 A1 | 6/2002 | Fraser |
| 2002/0107572 A1 | 8/2002 | Foley et al. |
| 2002/0151893 A1 | 10/2002 | Santilli |
| 2002/0193880 A1 | 12/2002 | Fraser |
| 2003/0028249 A1 | 2/2003 | Baccelli et al. |
| 2003/0109928 A1 | 6/2003 | Pasquet et al. |
| 2003/0167091 A1 | 9/2003 | Scharf |
| 2003/0195626 A1 | 10/2003 | Huppert |
| 2003/0195632 A1 | 10/2003 | Foley et al. |
| 2003/0204260 A1 | 10/2003 | Ferree |
| 2004/0073309 A1 | 4/2004 | Bianchi et al. |
| 2004/0127993 A1 | 7/2004 | Kast et al. |
| 2004/0127994 A1 | 7/2004 | Kast et al. |
| 2004/0148029 A1 | 7/2004 | Bianchi et al. |
| 2004/0162617 A1 | 8/2004 | Zucherman et al. |
| 2004/0172130 A1 | 9/2004 | Nakahara et al. |
| 2004/0199254 A1 | 10/2004 | Louis et al. |

2005/0038511 A1    2/2005   Martz et al.

FOREIGN PATENT DOCUMENTS

| | | |
|---|---|---|
| EP | 0 965 313 A1 | 12/1999 |
| EP | 0965313 A | 12/1999 |
| FR | 2 703 580 A1 | 10/1994 |
| FR | 2703580 A | 10/1994 |
| FR | 2 733 413 A1 | 10/1996 |
| FR | 2733413 A1 | 10/1996 |
| FR | 2747034 A | 10/1997 |
| FR | 2808995 | 11/2001 |
| FR | 2827156 | 1/2003 |
| WO | WO 9715248 | 5/1997 |
| WO | WO 98/01091 A1 | 1/1998 |
| WO | WO 9801091 A | 1/1998 |
| WO | WO 98/55052 * | 12/1998 |
| WO | WO 98/55052 A1 | 12/1998 |
| WO | WO 9855052 A | 12/1998 |
| WO | WO 99/09914 A1 | 3/1999 |
| WO | WO 9909914 A | 3/1999 |
| WO | WO9956676 A | 11/1999 |
| WO | WO 0187194 | 11/2001 |
| WO | WO 0300593 9 | 1/2003 |

OTHER PUBLICATIONS

FR 2 808 995 Preliminary Search Report, National Institute of Industrial Property (France), Jan. 29, 2001.
FR 2 827 156 Preliminary Search Report, National Institute of Industrial Property (France), Apr. 5, 2002.
Greffe et fusion, Website: http://www.ldrmedical.fr/roi.htm, Sep. 19, 2004.
Mc+ Le choix de l'ancrage, Website: http://www.ldrmedical.fr/mcplus.htm, Sep. 19, 2004.
PCT/FR01/01545, International Preliminary Examination Report, EPO, Aug. 30, 2002.
PCT/FR01/01545, International Search Report, EPO, Sep. 5, 2001.
PCT/IB02/03390, International Preliminary Examination Report, EPO, Nov. 6, 2003.
PCT/IB02/03390, International Search Report, EPO, Mar. 3, 2003.
ROI Privilegier la greffe en creant la chambre de fusion, Website: http://www.ldrmedical.fr/roi.htm, Sep. 19, 2004.

* cited by examiner

INTERSOMATIC CAGE WITH UNIFIED GRAFTS

FIELD OF INVENTION

The present invention relates to an intervertebral cage designed to be placed between two vertebrae to restore and/or maintain the intervertebral space, to replace the intervertebral disk. After the cage or implant has been placed, the intervertebral space is filled with autologous spongy bone or adapted bone substitutes. This invention also relates to instrumentation for placement of the intervertebral cage. Finally, it also relates to a pair of intervertebral cages of this type.

BACKGROUND ART

Prior art has already described intervertebral cages, for example Stryker cages. These cages are parallelepiped-shaped, the bottom and the top of the cage being completely open, the side and top openings will be placed facing the two vertebrae that are to be kept at a distance from each other. Spongy bone is then compacted inside the cage to finally cause fusion of the bone (or arthrodesis) of the two vertebrae separated by a suitable disk space.

For posterior placement, there are usually two cages adjacent to each other at a distance from each other in the intervertebral space, and the graft is firstly compacted inside the two cages and secondly the space between the two cages is filled in by spongy bone or bone substitute.

It is found that the growths of the three independent grafts (two inside the cages and one between the cages) vary with respect to each other. In particular, the graft placed between the cages contributes more quickly to the fusion than the compacted grafts inside the cages. Obviously, this is a disadvantage, particularly with regard to the stability of the grafts and the two vertebrae held in place by these grafts, and concerning the time necessary to obtain good stability.

Document WO/98/55052 also discloses intervertebral cages.

In the first case, they are composed of a main very thick curved part particularly with a thickness that increases from the middle towards the ends. Therefore, these cages are complicated to make due to their curved shape.

In the second case, they are composed of a straight main part and return parts each being prolonged by an end part that together form a small interval less than 25% of the longitudinal extension of the internal housing of the cage.

SUMMARY OF THE INVENTION

The present invention overcomes the disadvantages mentioned above by proposing an intervertebral cage that enables good growth of the graft or grafts placed between the vertebrae and is each to make, particularly due to the fact that it has straight longitudinal walls, and has good resistance to compression forces applied by the vertebral plates, particularly in the case of posterior implantation in which two intervertebral cages are placed side by side at a distance from each other.

According to the invention, the intervertebral cage is composed of a thin main wall prolonged by two return parts, the thin main wall having an approximately constant thickness and each return part being extended by an end part, the end parts facing each other with a gap between them, the wall, the return parts and the end part delimiting an inner cavity, the extension of the clear gap parallel to the straight wall being between 50% and 100% of the largest dimension of the cavity parallel to the wall, and preferably between 70% and 90%.

Thus, according to the invention, the intervertebral cage comprises only three walls, namely the straight main wall and the two return parts prolonged by the end parts, such that the graft that was compacted on the inside of each cage before the cage was placed (in the case of posterior placement in which two cages are used arranged side by side and at a spacing from each other), and the graft that is made to grow between the two cages are all three in mutual contact, such that there is actually only a single graft which will therefore grow homogeneously to obtain an optimum contact between the vertebral plate—graft—vertebral plate, in other words a good homogeneous and stable contact, also making the cage more resistant even though it only has one straight main wall and a large gap between the end parts.

The applicant realized before anyone else that in the case in which there is a main part in the form of a straight wall, it is still possible to significantly move the end parts away from the return parts without endangering the stability and the strength of the intervertebral cages between the vertebral plates. The applicant believes that the fact that the central graft and the compacted grafts in the internal parts of the two cages arranged with their openings facing each other fuse together well and helps to make the two cages more resistant to the tension forces exerted by the vertebral plates, and it is therefore possible to increase the air gap between the end parts, although the main part is only a thin single straight wall; but this is only a hypothesis that the applicant cannot confirm.

According to one preferred embodiment of the invention, the thin main wall is a straight wall.

According to one advantageous embodiment, the thickness of the end parts is the same as the thickness of the thin main wall.

According to one advantageous embodiment, the thickness of the thin main wall is between 1 mm and 5 mm and preferably between 2 mm and 4 mm, for example 3 mm.

According to one advantageous embodiment, the end part that projects from the largest return part is provided with at least one hole, and preferably two holes on the front face facing the other end part, and the other return part comprises a threaded hole on its part external to the ring, these holes being designed to cooperate with pins associated with placement instrumentation for placement of the implant or the intervertebral cage in the intervertebral space.

The present invention also relates to instrumentation for placement of an intervertebral cage, particularly by posterior placement.

According to the invention, the instrumentation for placement of an intervertebral cage between two vertebrae in the disk space comprises a rod that will cooperate with associated coupling means formed in an outer surface of the intervertebral cage.

According to one improvement of the invention, the instrumentation comprises a prolonged part in the form of a rectangular or slightly curved wall, on the distal end of the rod, the dimensions and position of which are such that the wall closes off the clear gap between the two end parts, when the rod is in a position to cooperate with the coupling means.

The rectangular wall replaces the "missing wall" of the cage during placement, firstly to retain the graft that was compacted inside the cage before the cage was put into position, and secondly to make the assembly stiffer to facilitate its placement in the intervertebral space.

For example, coupling means are composed of a hole formed in the outer surface of the cage, the hole being sized such that the rod can be inserted inside it.

According to the invention, it is also possible to use blocking means that will block mutual rotation of the cage and the instrumentation in the position in which the rod and the coupling means cooperate with each other.

For example, these blocking means may be composed such that the shape of the periphery of the hole is made hexagonal or to have at least one flat, and one end of the rod has a matching shape.

According to one improvement of the invention, attachment means designed to fix the rod to the coupling means may also be provided. These attachment means, which in particular can be released, are used to insert the cage such that it cannot accidentally stop cooperating with the rod.

For example, these attachment means may consist of tapping the hole and providing an associated thread at the distal end of the rod. In this case, the tapping in the hole and the thread on the rod also form blocking means.

According to one improvement to the invention, the outside distal edge of the wall comprises two pins that can penetrate into the holes formed in the face on the end part of the cage.

According to the invention, the wall is offset with respect to the centre line of the main rod, particularly by a distance equivalent to half of the dimension of the return part at the rod end.

The invention also relates to a pair of intervertebral cages according to the invention, in particular the two intervertebral cages of the pair being symmetric with each other like in a mirror.

The drawings, given solely as examples of one embodiment of an intervertebral cage according to the invention and instrumentation used for placement in the intervertebral space, are described.

DETAILED DESCRIPTION OF THE DRAWING

Figure 1:
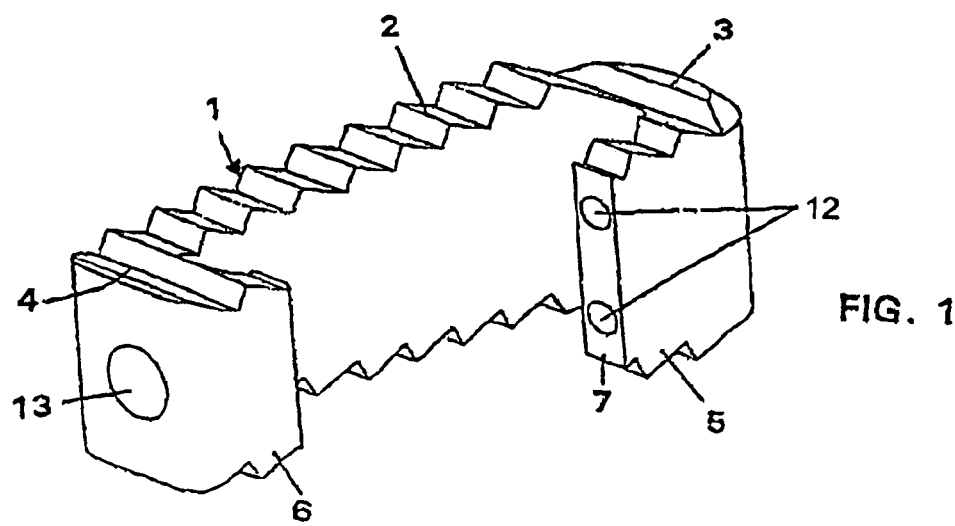
FIG. 1 is a perspective view of an intervertebral cage according to the invention.

FIG. 1 shows in intervertebral cage 1 according to the invention The intervertebral cage comprises a main wall 2 from which two return parts 3 and 4 project. The two return parts 3 and 4 are prolonged by a first end part 5 and a second end part 6 respectively The two end parts 5 and 6 are approximately parallel to the main wall 2. The wall 2, the return parts 3 and 4 and the end parts 5, 6 delimit an inner cavity 30 in the cage, by prolonging the two end parts towards each other.

The two end parts 5, 6, are at a distance from each other and there is a clear gap between them. The clear gap extends along the direction of the length parallel to the main wall 2 over a length equal to 78% of the longest length of the inner cavity 30.

Figure 2:
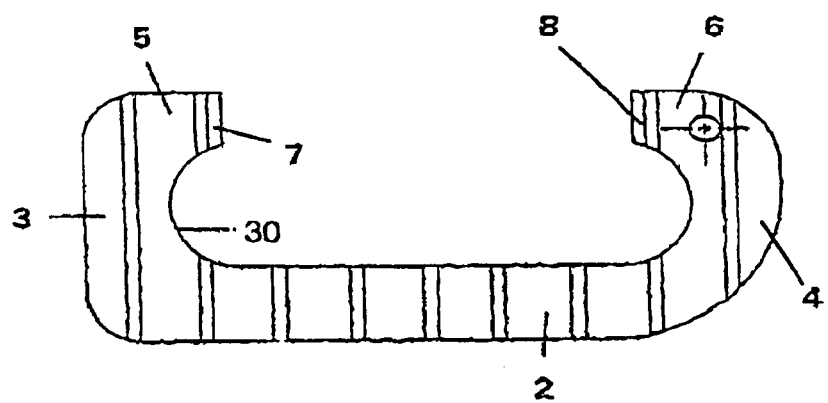
FIG. 2 is a longitudinal sectional view from the top of the intervertebral cage of FIG. 1.

The two end parts 5, 6 face each other through a first end face 7 and a second end face 8. The main wall 2 is 3 mm thick. The thickness of the end walls is the same as the thickness of the main wall 2. The two return parts 3 and 4 are approximately perpendicular to the main wall 2. The two end parts 5 and 6 extend from the return parts 3 and 4 that are approximately perpendicular to the end parts, parallel to the main wall 2, such that the shape of the cage 1 forming the intervertebral cage is approximately like a C with a straight back in the cross-sectional plane (see FIG. 2).

The upper edge 9 and the lower edge 10 of the ring forming the intervertebral cage have a toothed shape 11. These teeth or notches give good anchorage of the cage in the vertebral plates.

Two holes 12 are formed in face 8, facing the end part 5. A tapped hole 13 is formed in the outside edge of the return part 4.

Figure 4:
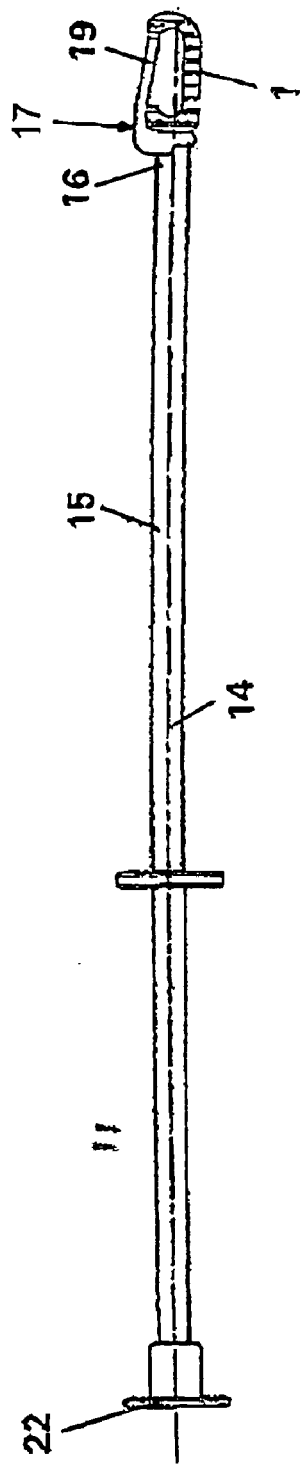
FIG. 4 shows instrumentation for placement of an intervertebral cage according to the invention, and also shows the intervertebral cage shown in FIG. 1.
Figure 5:
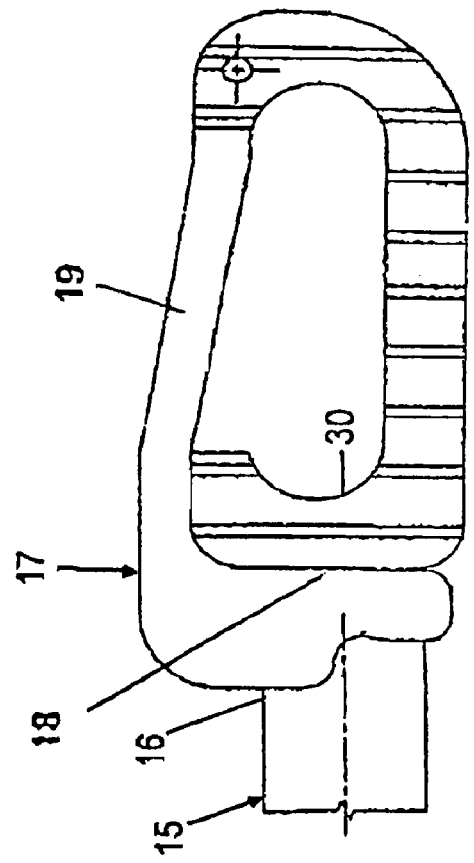
FIG. 5 is an enlarged view of part of FIG. 4.
Figure 6:
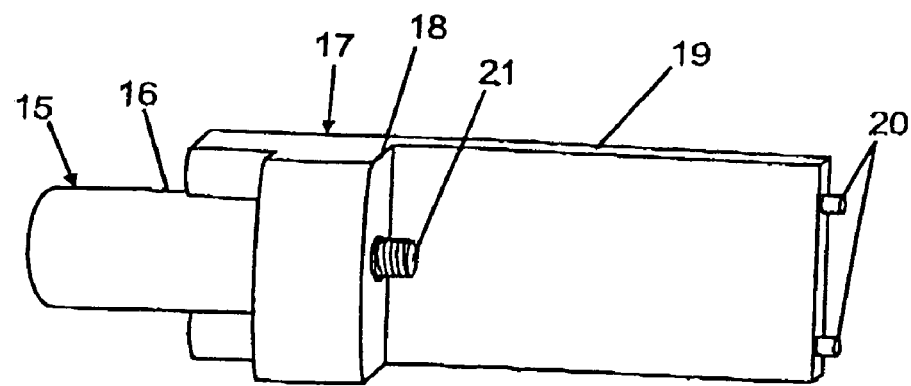
FIG. 6 is a perspective view of the enlarged part of the instrumentation of FIG. 4, without showing the intervertebral cage of FIG. 1.

These holes 12 and 13 are designed to cooperate, respectively, with the pins 20 and the threaded end 21 of the rod 15 of an instrument 14 for the placement of a thin type intervertebral cage between the two vertebrae, particularly by posterior placement. In particular, this instrumentation 14 is shown in FIGS. 4 to 6.

It comprises a hollow rod 15 that is extended at its end 16 by a part 17 in the form of a wedge comprising a surface 18 perpendicular to the centre line of the rod 15 and a wall 19 forming an angle of about 75° from the surface 18. The shape of the wall 19 is rectangular. The angle between the wall 19 and the surface 18 depends on the extended length of the clear gap. It is designed such that the wall 19 completely fills the opening between the two end parts 5 and 6.

Figure 7:
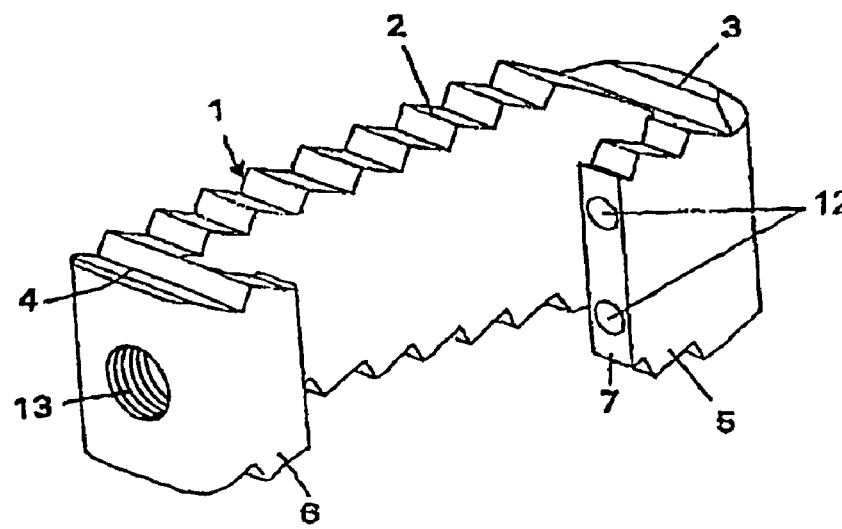
FIG. 7 is a perspective view of the intervertebral cage of FIG. 1 showing an attachment structure.
Figure 8:
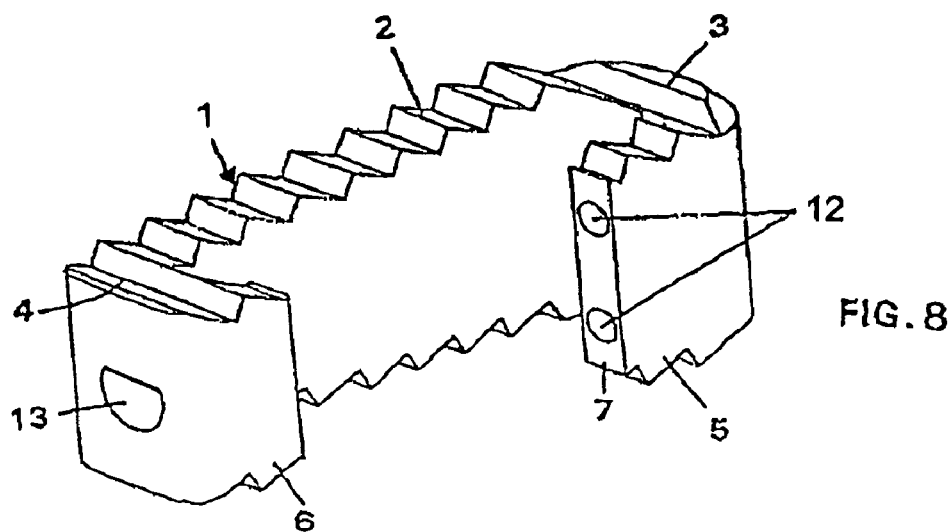
FIG. 8 is a perspective view of the intervertebral cage of FIG. 1 showing a blocking structure.

On its edge opposite the rod 15, the plate or wall 19 comprises two pins 20 designed to cooperate with holes formed in the face 8 of the intervertebral cage 1. The instrumentation 14 also comprises a threaded end 21 (FIG. 6) of the rod 15 that will cooperate with the tapped hole 13 (FIG. 7) formed in the outside part of the return part 4 of the intervertebral cage. This threaded end 21 extends inside the rod 15 and opens up at the end 16 of this rod 15, at the surface 18 through a hole formed in it. The user screws and unscrews the threaded rod using the manoeuvring handle 22. Screwing the rod in firstly blocks the rod and the cage in rotation, and secondly fixes the rod to the cage.

The length of the plate 29 is approximately equivalent to the length of the main wall 2 of the intervertebral cage, such that when the threaded end 21 is screwed into the tapped hole 13, pins 20 (FIG. 7) penetrate into the holes 12. It is thus possible to insert the intervertebral cage between two vertebrae and then to remove the instrumentation. The two sides 7 and 8 facing the end parts 5 and 6 are offset from each other by a dimension corresponding to the thickness of the plate 19.

The wall 19 replaces the "missing wall" of the cage during placement, firstly to fix the position of the graft that was compacted in the cage before its placement, and secondly to make the assembly stiffer to facilitate its placement in the intervertebral space.

Figure 3:
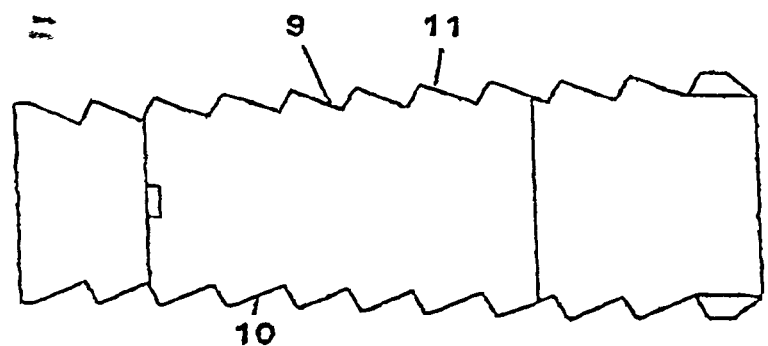
FIG. 3 is a side view of the intervertebral cage in FIG. 1.

Finally, the cage may be bevelled in the longitudinal direction (see FIG. 3). This bevelled shape makes it possible to restore the lordosis.

The invention claimed is:

1. An intervertebral cage configured for insertion between an upper vertebra and a lower vertebra, comprising:
   an elongated main wall having first and second opposing ends thereof;
   a first return part extending away from the first end of the main wall;
   a second return part extending away from the second end of the main wall;
   a first end part extending from the first return part and terminating at a first end face;
   a second end part extending from the second return part and terminating at a second end face;
   a substantially planar upper surface configured for contact with the upper vertebra, the upper surface comprising teeth and at least portions of the main wall, the first return part, the second return part, the first end part, and the second end part;
   a substantially planar lower surface configured for contact with the lower vertebra, the lower surface comprising teeth and at least portions of the main wall, the first return part, the second return part, the first end part, and the second end part;
   a gap formed between the first end face and the second end face, the gap open at the upper surface and the lower surface and extending therebetween so that the first end part and the second end part are connected only through the first return part, the second return part, and the main wall;
   a cavity delimited by the main wall, the first return part, the second return part, the first end part, and the second end part, the cavity open along the upper surface and the lower surface, with the intervertebral cage opened to the cavity along the gap;
   a coupler for a placement instrument adapted to place the cage between the upper and lower vertebrae; and
   an instrument for inserting the cage between the upper and lower vertebrae, the instrument comprising a rod attachable to the coupler, a first outward curved portion adapted to reach around the second end part of the cage, and a second incurvate portion attached to the first outward curved portion, the second incurvate portion adapted to close the gap and couple with the first end face.

2. The intervertebral cage of claim 1 in which the main wall is substantially straight.

3. The intervertebral cage of claim 2 in which the main wall has a substantially constant thickness between the upper and lower surface.

4. The intervertebral cage of claim 3 in which the main wall and the first and second end parts have substantially the same thickness.

5. The intervertebral cage of claim 1 in which the first end face and the second end face are substantially flat and substantially parallel.

6. The intervertebral cage of claim 1 wherein the gap extends substantially parallel to the main wall and corresponds to between 100% and about 50% of the largest dimension of the cavity parallel to the main wall.

7. The intervertebral cage of claim 1 wherein the gap extends substantially parallel to the main wall and corresponds to between about 90% and about 70% of the largest dimension of the cavity parallel to the main wall.

8. The intervertebral cage of claim 1 further comprising a longitudinal bevel adapted to restore a lordosis.

9. The intervertebral cage of claim 1 in which the teeth of the upper surface and the lower each extend along the main wall, the first return part, the second return part, the first end part, and the second end part.

10. The intervertebral cage of claim 1 in which the second incurvate portion comprises a wall adapted to extend at least partially into the gap and to close the gap between the first and second end faces.

11. The intervertebral cage and instrument of claim 10 wherein the instrument wall is offset from a center line of the rod.

12. The intervertebral cage and instrument of claim 10 further comprising a blocking structure adapted to block rotation of the cage.

13. The intervertebral cage and instrument of claim 12 wherein the blocking structure comprises at least one flat part matching a flat part at the end of the rod.

14. The intervertebral cage and instrument of claim 13 wherein the blocking structure comprises matching hexagonal peripheries.

15. The intervertebral cage and instrument of claim 10 wherein the coupler includes a hole disposed in the cage adapted to receive a portion of the rod.

16. The intervertebral cage and instrument of claim 15 further comprising a blocking structure integral with the coupler, wherein the hole disposed in the cage is tapped and the portion of the rod received in the hole is threaded.

17. An intervertebral cage configured for insertion between an upper vertebra and a lower vertebra, comprising:
   an elongated main wall having first and second opposing ends thereof;
   a first return part extending away from the first end of the main wall;
   a second return part extending away from the second end of the main wall;
   a first end part extending from the first return part and terminating at a first end face;
   a second end part extending from the second return part and terminating at a second end face;
   a substantially planar upper surface configured for contact with the upper vertebra, the upper surface comprising teeth and at least portions of the main wall, the first return part, the second return part, the first end part, and the second end part;
   a substantially planar lower surface configured for contact with the lower vertebra, the lower surface comprising teeth and at least portions of the main wall, the first return part, the second return part, the first end part, and the second end part;
   a gap formed between the first end face and the second end face, the gap open at the upper surface and the lower surface and extending therebetween so that the first end part and the second end part are connected only through the first return part, the second return part, and the main wall;
   a cavity delimited by the main wall, the first return part, the second return part, the first end part, and the second end part, the cavity open along the upper surface and the lower surface, with the intervertebral cage opened to the cavity along the gap;
   a coupler for a placement instrument adapted to place the cage between the upper and lower vertebrae; and an instrument for inserting the cage between the upper and lower vertebrae, the instrument comprising a rod attachable to the coupler and an instrument wall adapted to extend at least partially into the gap and to close the gap between the first and second end faces, wherein the instrument wall has at least two pins adapted to penetrate into holes formed in the first end face.

18. The intervertebral cage and instrument of claim 17 wherein the instrument wall is offset from a center line of the rod.

19. The intervertebral cage and instrument of claim 17 further comprising a blocking structure adapted to block rotation of the cage.

20. The intervertebral cage and instrument of claim 19 wherein the blocking structure comprises at least one flat part matching a flat part at the end of the rod.

21. The intervertebral cage and instrument of claim 20 wherein the blocking structure comprises matching hexagonal peripheries.

22. The intervertebral cage and instrument of claim 17 wherein the coupler includes a hole disposed in the cage adapted to receive a portion of the rod.

23. The intervertebral cage and instrument of claim 22 further comprising a blocking structure integral with the coupler, wherein the hole disposed in the cage is tapped and the portion of the rod received in the hole is threaded.

* * * * *